United States Patent [19]

Chou

[11] Patent Number: 4,562,209

[45] Date of Patent: Dec. 31, 1985

[54] PROMOTION OF FEED EFFICIENCY IN ANIMALS

[75] Inventor: Billy J. Chou, Paoli, Pa.

[73] Assignee: William H. Rorer, Inc., Fort Washington, Pa.

[21] Appl. No.: 425,093

[22] PCT Filed: Aug. 24, 1981

[86] PCT No.: PCT/US81/01145

§ 371 Date: Jul. 1, 1982

§ 102(e) Date: Jul. 1, 1982

[87] PCT Pub. No.: WO83/00624

PCT Pub. Date: Mar. 3, 1983

Related U.S. Application Data

[63] Continuation-in-part of Ser. No. 109,848, Jan. 7, 1980, abandoned.

[51] Int. Cl.$^4$ ............................................. A61K 31/17
[52] U.S. Cl. .................................. 514/596; 514/597; 514/598
[58] Field of Search .......................................... 424/322

[56] References Cited

U.S. PATENT DOCUMENTS

| | | | |
|---|---|---|---|
| 3,796,797 | 3/1974 | Parish et al. | 424/18 D |
| 3,914,245 | 10/1975 | Gall | 260/308 B |
| 3,933,794 | 1/1976 | Hester et al. | 260/239 BD |
| 4,060,635 | 11/1977 | Diamond et al. | 424/322 |
| 4,219,567 | 8/1980 | Diamond et al. | 424/322 |
| 4,440,765 | 4/1984 | Diamond et al. | 424/322 |

*Primary Examiner*—Frederick E. Waddell
*Attorney, Agent, or Firm*—James A. Nicholson; Alexis Barron; Martin F. Savitzky

[57] ABSTRACT

Feed supplements, which increase the dwell time of ingested nutrient matter in the gastrointestinal tract of food producing animals, and which provide for increased digestion and absorption of ingested nutrient matter, are administered to food producing animals to increase feed efficiency.

6 Claims, No Drawings

PROMOTION OF FEED EFFICIENCY IN ANIMALS

This application is a continuation-in-part of application Ser. No. 109,848 filed Jan. 7, 1980 now abandoned.

FIELD OF THE INVENTION

This invention relates to the field of agents used in promoting feed efficiency in animals, particularly when administered as feed additives, and to a method for promoting the growth rate of food-producing animals, especially livestock and poultry, for increasing animal products, for example, milk production in mammalian species and egg production in avian species.

It is generally accepted that the meat, poultry dairy and cultivated fishing industries provide the most inefficient source of food for human consumption. These industries use feed sources (for example, grains, fruits, and vegetables) which are also a primary source of nutrients for humans. The production of livestock, poultry and cultivated fish entails the consumption of more primary source protein and carbohydrates fit for human consumption than is replaced by that of the resultant animal. In addition to the actual reduction in primary source foods for human consumption created by these industries, the cost of protein and carbohydrate supplied for human consumption through secondary sources is substantially magnified. In view of these considerations, there is need for improvement in the utilization of animal feed in the raising of animals as secondary food sources.

REPORTED DEVELOPMENTS

A number of synthetic chemical compositions and naturally occurring materials have been utilized to increase the growth rate of animals and to decrease the consumption of animal foodstuff. These agents fall into a number of categories, including: antibacterials, such as, sulfa drugs and antibiotics; parasitic prophylaxis; metabolic drugs; sedatives or tranquilizers; and, in ruminants, nitrogen supplements and rumen bacterial respiration modifiers.

The antibacterials are effective by reducing the incidence of bacterial disease in the animal population.

The antiparasitic agents are effective in reducing the incidence of parasitic infection.

Metabolic drugs increase metabolic synthesis of protein and include the hormones, such as, estrogens, progesterone and diethylstilbesterol.

Sedatives and tranquilizers effect a reduction in animal movement and hyperactivity resulting in greater protein synthesis and weight retention. Sedatives and tranquilizers of the triazole and benzdiazepine class of compounds have been disclosed as useful in U.S. Pat. Nos. 3,914,245 to Gall et al and 3,933,794 to Hester et al.

Ruminant feed containing supplemental nitrogen enhance protein synthesis. Nitrogen supplements have been disclosed in U.S. Pat. Nos.: 3,989,846 to Helgerson (slow release urea composition); 3,843,799 to Elofson et al (complex glucosylurea converted to ammonia in rumen); and 4,044,156 to Diner et al (monoglucoxyl ureide). Ruminant feed supplements which are formulated to be resistant to microbial breakdown in the rumen, but not resistant to substantial digestive breakdown in the abomasum and intestines have been disclosed in U.S. Pat. Nos.: 3,988,480 to Ames et al; 3,959,493 to Ballsrud et al; 4,001,390 to Fildes; and 3,562,806 to Grant et al.

Rumen bacterial respiration modifiers act through an effect on the bacterial population ordinarily present in the animals' digestive system and reduce the amount of bacterial products which are not absorbed by the ruminant. Feed supplements for ruminants which influence the O-R potential of microfloral respiration in the rumen have been disclosed as feed efficiency agents in U.S. Pat. No. 2,808,332 to Anderson et al. The reduction of gaseous waste production in ruminates has been reported in U.S. Pat. No. 3,801,710 to Parish et al which discloses the administration to ruminates of certain haloalkehyde sulfonates and phosphonates. U.S. Pat. No. 3,796,797 to Parish discloses the administration to ruminants of a chloral molasses feed.

Other agents, such as the anticholinergics have also been used.

Most of these known growth promotants can have undesired side effects. The antibacterials and antiparasitics pose the problem that their use will result in resistant strains of disease-causing bacteria. Hormonal agents can also produce unwanted side effects, and in some cases, such agents have been shown to be carcinogenic. Sedatives and tranquilizers can leave undesirable residues in the animal. The effectiveness of anticholinergics is limited due to the undesirable side effects manifested when therapeutic doses are administered.

The present-invention is directed to improved means for effecting feed efficiency in animals.

SUMMARY OF THE INVENTION

This invention relates to feed efficiency supplements, feed additive compositions, a method for increasing the feeding efficiency of animals, and, in particular, a method for increasing the digestive absorption of nutrients in an animal to increase said animal's feed efficiency and comprises administering to an animal for assimilation by the animal a material which increases the dwell time of nutrient matter in the digestive tract of said animal, the administration of said material being for a period of time sufficient to effect an increase in the digestion and absorption of said nutrients over and above that which would have been effected had the animal not assimilated said material.

Numerous benefits are achieved as a result of the use of the present invention. Efficient utilization of animal feed is realized without the adverse side effects that accompany the use of other growth promotants. Use of the present invention results not only in a reduction in consumption of animal feed, but also in a reduction in waste generation owing to a more efficient digestive process.

Particularly preferred materials for use in the method of this invention comprise, for example, amidinoureas having antimotility properties, diphenoxylates and loperamide. The most preferred feed efficiency agents are phenyl substituted amidinoureas having antimotility properties.

Another aspect of this invention relates to the shortening of the period of growth from infancy to maturity in animals which produce food or to increasing the production of development of animal products by administering to the animals during its growth stages an effective amount of an antimotility agent.

Still another aspect of this invention relates to a method for increasing the feed conversion ratio of a healthy feeding animal.

DETAILED DESCRIPTION OF THE INVENTION

It has been found that compositions containing certain antimotility agents are effective in lowering the unit amount of food consumed by feeding animals per unit increase in animal production output, such as, body weight, milk production, egg production or fur production. In standard laboratory screening tests, described more fully below, certain antimotility agents have been shown to be effective in increasing the residence time of ingested food, and effecting a corresponding increase in the amount of digestible material actually digested and absorbed by the test animals.

A particular class of compounds for use in practicing the invention are amidinoureas having antimotility properties. For example, the amidinoureas defined below are readily absorbed through the intestinal wall of mammals and fowl, and may be administered as compositions formulated as tablets, capsules, powders or liquids suitable for either direct oral administration or in combination with animal feed. The antimotility agents used to increase feed efficiency can, if desired, be used in combination with other food additives such as growth promoters, compositions for providing electrolyte balance, agents for improving taste, smell, texture and the like, or with therapeutic agents such as sulphonamides, sulphones, antibiotics, hormones, or with other suitable excipients.

Compounds within the broad class of compounds which are useful in the practice of the present invention are known in the art for the purpose of treating certain veterinary diseases, such as, scours, by administering such compounds for limited periods of time at therapeutic dosages to counter the disease. In contrast, the present invention relates to the continuous feeding or the feeding on a regular basis of a non-therapeutic dosage of a feed efficiency agent irrespective of the presence of any veterinary disease in the animal and for an extended period of time. In normal use, this invention is practiced on a large number of healthy feeding animals, such as a herd of cattle or a flock of sheep, instead of selectively administering a therapeutic dose of compound to sickly members of the animal group.

Amidinoureas suitable for use in this invention and which can be used as the principal active ingredient in the feed efficiency compositions of this invention are compounds of the formula:

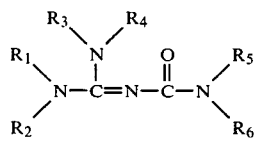
I wherein one of $R_1$ or $R_5$ is phenyl, phenyl in which one or more of the hydrogens is substituted by halo, lower alkyl, halo lower alkyl, nitro, lower alkoxy, hydroxy, aryl lower alkoxy, acyloxy, cyano, halo lower alkoxy, or lower alkyl sulfonyl; aralkyl, heterocycle, or heterocycle having one or more of the hydrogens replaced by lower alkyl, lower alkoxy, halo, halo lower alkyl, amino, nitro, hydroxy, cyano, carboxyl or lower alkyl sulfonyl; and the other of $R_1$ or $R_5$ is hydrogen, lower alkyl, lower alkoxy, lower alkenyl, cyclo lower alkenyl, cyclo lower alkyl, aralkyl, lower alkenyl, halo alkyl, hydroxy lower alkyl, lower alkoxy lower alkyl, cyano lower alkyl, amino lower alkyl, mono- or di-lower alkyl amino lower alkyl, carbamoyl lower alkyl, mono- or di-carbamoyl lower alkyl, lower alkoxy carbamoyl lower alkyl, aralkoxy carbamoyl lower alkyl, acyl lower alkyl, alkyl sulfonyl or aralkyl sulfonyl; $R_2$ and $R_6$ are each independently selected from the group consisting of hydrogen, lower alkyl, lower alkoxy, lower alkenyl, cyclo lower alkenyl, cyclo lower alkyl, aralkyl, lower alkynyl, halo alkyl, hydroxy lower alkyl, lower alkoxy lower alkyl, cyano lower alkyl, amino lower alkyl, mono- or di-lower alkyl amino lower alkyl, carbamoyl lower alkyl, mono- or di-carbamoyl lower alkyl, lower alkoxy carbamoyl lower alkyl, aralkoxy carbamoyl lower alkyl, acyl lower alkyl, alkyl sulfonyl or aralkyl sulfonyl; and when $R_1$ is phenyl, phenyl substituted as above, aralkyl, heterocycle or heterocycle substituted as above, $R_5$ together with $R_6$ and the nitrogen to which $R_5$ and $R_6$ are attached may form a 5 or 6 membered heterocyclic ring which may include 0 to 2 additional hetero atoms which may be either oxygen, nitrogen or sulfur; and when $R_5$ is phenyl, phenyl substituted as above, aralkyl, heterocycle or heterocycle substituted as above, either $R_1$ and $R_2$ together with the nitrogen to which they are attached, or $R_1$ and $R_3$ together with the nitrogen to which they are attached, may be a 5, 6, 7 or 8 membered heterocyclic ring which may include 0 to 2 additional hetero atoms which may be either oxygen, nitrogen or sulfur; and $R_3$ and $R_4$ are each independently hydrogen, lower alkyl, lower alkoxy, lower alkenyl, lower alkynyl, cyclo lower alkyl or aralkyl; and their pharmaceutically acceptable acid addition salts.

It should be understood that whereas the structure of the amidinoureas are shown here in a particular configuration for purposes of illustration, these compounds may exist in various enolized or tautomeric forms, particularly where one or $R_3$ and $R_4$ is hydrogen, shown, for example, by the following formula:

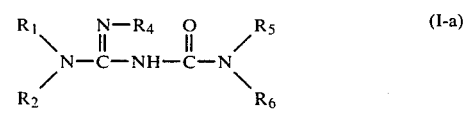
(I-a)

Certain of the compounds can also be obtained as hydrates or in different polymorphic forms. The structures used herein to designate the useful compounds are intended to include the compound shown along with its alternative or transient states.

As employed above and throughout the disclosure, the following terms unless otherwise indicated shall be understood to have the following meanings:

"Alkyl" means a saturated aliphatic hydrocarbon which may be either straight or branched chain. Lower alkyl groups are preferred.

"Lower alkyl" means an alkyl group as above, having about 1 to about 6 carbon atoms. Suitable lower alkyl groups are methyl, ethyl, propyl, isopropyl, butyl, sec-butyl, tert-butyl, pentyl, and isopentyl.

"Cycloalkyl" means an aliphatic monocyclic saturated carbocyclic group. Preferred groups have about 3 to about 6 carbon atoms, for example, cyclopropyl, cyclopentyl and cyclohexyl.

"Alkenyl" means an unsaturated aliphatic hydrocarbon containing one or more double bonds and may be straight or branched chain. Lower alkenyl are preferred.

"Lower alkenyl" means alkenyl of about 2 to about 6 carbon atoms, such as, ethylene, propylene, butylene, isobutylene, etc.

"Alkynyl" means an unsaturated aliphatic hydrocarbon containing one or more triple bonds. Lower alkynyl groups are preferred.

"Lower alkynyl" means alkynyl of about 2 to about 6 carbon atoms, such as, propargyl, butynyl, pentynyl, etc.

"Aryl" is an aromatic radical group and includes phenyl and substituted phenyl. Phenyl and substituted phenyl groups are preferred.

"Substituted phenyl" means a phenyl group in which one or more of the hydrogens has been replaced by the same or different substituents including halo, carboxyl, lower alkyl, halo lower alkyl, nitro, amino, acylamino, hydroxy, lower alkoxy, aryl lower alkoxy, acyloxy, cyano, halo lower alkoxy or lower alkyl sulfonyl.

"Aralkyl" means an alkyl (preferably a lower alkyl) in which one or more hydrogens is substituted by aryl, for example, benzyl or phenethyl.

"Heterocycle" means a 5 to 8 membered ring having about 1 to about 3 hetero atoms which may be nitrogen, oxygen or sulfur, including pyridyl, 2-pyridyl or 3-pyridyl; pyrimidyl, pyrazolyl, imidazolyl, furyl, thienyl, oxazolyl, thiazolyl, piperidyl, piperazenyl, morpholinyl, thiomorpholinyl and diazipinyl. Pyridyl groups are preferred.

"Substituted heterocycle" means a heterocycle in which one or more of the hydrogens on the ring carbons have been replaced by substituents as given above with respect to substituted phenyl.

The terms "halo" and "halogen" include all four halogens; namely, fluorine, chlorine, bromine and iodine.

"Halo alkyl" and "halophenyl" include alkyl or phenyl groups having one or more halo substituents which may be the same or different, such as trifluoromethyl, 1-chloro-2-bromoethyl, chlorophenyl, 2-chloro-6-bromophenyl, etc.

The term "acyl" means a radical of the formula RCO, wherein R is an organic radical, such as lower alkanoyl or aroyl. In lower alkanoyl, R is alkyl, as in acetyl and propionyl, and in aroyl, R is aryl, as in benzoyl.

The term "acyloxy" means an organic acid radical of the formula RCOO wherein R is an organic radical, such as acetoxy, propionoxy or benzoyloxy.

The term "acylamino" means an organic amido group of the formula

```
RCONH
  |
``` where R is an organic alkyl group, preferably lower alkyl.

The term "lower alkanoyl" means the acid radical of a lower alkanoic acid, such as acetyl or propionyl.

Among the amidinoureas of Formula I, a particularly preferred group of amidinoureas suitable for use in the composition and method of this invention are those in which the $R_5$ or $R_1$ substituent is a phenyl or substituted phenyl. A subclass of these compounds, of particular interest, are where the phenyl substituents are in the 2 and 6 positions (i.e., ortho to the carbon attached to the urea nitrogen). Such preferred compounds can be represented by the formulae:

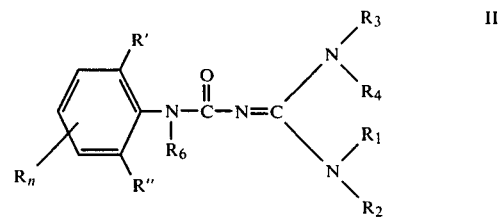

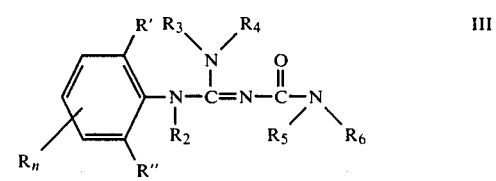

Particularly preferred compounds of Formulae I, II and III are those wherein the R' and R" phenyl substituents are lower alkyl, halo lower alkyl, lower alkoxy or halo and at least one of the $R_1$, $R_2$, $R_3$, $R_4$ and $R_5$ is hydrogen. The preferred lower alkyl substituents are methyl, ethyl, propyl and isopropyl. The preferred halo substituents are chlorine and bromine. The preferred halo lower alkyl substituents are chloromethyl and trifluoromethyl.

A most preferred group of amidinoureas suitable for use in the practice of this invention are the compounds of the formulae:

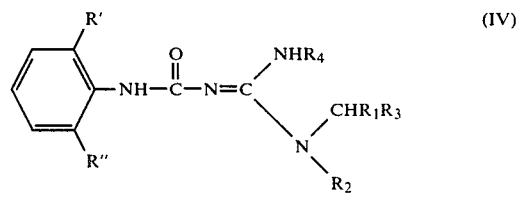

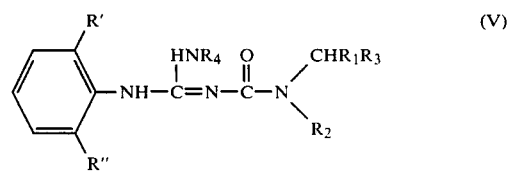

wherein $R_1$, $R_2$, $R_3$ and $R_4$ are each hydrogen, lower alkyl, lower alkoxy or hydroxy; and R' and R" are each hydrogen, halo or lower alkyl.

The compounds of Formulae I to V can be used in the practice of this invention in the form of the base or as salts which may be prepared by reacting these compounds with pharmaceutically acceptable acids. Suitable acid addition salts are, for example, the salts derived from the following organic and inorganic acids: hydrochloric acid, nitric acid, sulfuric acid, phosphorous acid, orthophosphoric acid, etc.; aliphatic mono- and dicarboxylic acids such as acetic acid, propionic acid, succinic acid, formic acid, caprylic acid, maleic acid, oxalic acid, malonic acid, etc.; phenyl-substituted alkanoic acids, hydroxy alkanoic acids, aromatic carboxylic acids, and aliphatic and aromatic sulfonic acids such as methylbenzoic acid, phthalic acid, benzenesulfonic acid, phenylpropionate, tartaric acid, citric acid, lactic acid, glycollic acid, phenylacetic acid, phenylbutyric acid, methane sulfonic acid, etc.

Suitable amidinoureas for use as feed efficiency supplements are also those disclosed in the *Arzneimittel Forschung*, 28 (II), 1433-1480 (1978) and in U.S. Pat. Nos. 4,115,647; 4,088,785; 4,025,652; 4,115,564; 4,060,633; 4,246,409; 4,058,557 and 4,147,804, the disclosures of which are incorporated herein by reference.

The amidinoureas employed as principal active ingredients in the compositions and methods of this invention are prepared by methods known in the art, as disclosed in the incorporated references noted above.

Exemplary compounds prepared in accordance with such teachings for utilization in this invention are named below wherein the urea nitrogens are designed as positions 1 and 3:

1-(2,6-dimethylphenyl)-3-methylamidinourea
O-chlorophenylamidinourea
(2,3-dichlorophenylamidino)urea
(2,4-dichlorophenylamidino)urea
(2,5-dichlorophenylamidino)urea
1-(2',6'-dimethylphenyl)-3-(1',1',3',3'-tetramethylamidino)-urea
(3,4-dichlorophenylamidino)urea
(3,5-dichlorophenylamidino)urea
(2,6-dichlorophenylamidino)urea
m-chlorophenylamidinourea
p-chlorophenylamidinourea
3,4-difluorophenylamidinourea
m-bromophenylamidinourea
p-bromophenylamidinourea
3,4-dibromophenylamidinourea
3-chloro-4-bromophenylamidinourea
3-bromo-4-chlorophenylamidinourea
3-chloro-4-fluorophenylamidinourea
3-bromo-4-fluorophenylamidinourea
3-fluoro-4-chlorophenylamidinourea
2,6-dimethylphenylamidinourea
2,6-diethylphenylamidinourea
2-methyl-6-ethylphenylamidinourea
2-methyl-6-methoxyphenylamidinourea
2-methyl-6-ethoxyphenylamidinourea
2-ethyl-6-ethoxyphenylamidinourea
3,4-dimethoxyphenylamidinourea
3,4-dihydroxyphenylamidinourea
3,4,5-trimethoxyphenylamidinourea
3,4,5-trihydroxyphenylamidinourea
1-(2,6-dimethylphenylamidino)-3,3-(N-methyl-3'-azapentamethylene)urea
1-(2,6-dimethylphenylamidino)-3,3-(N-methyl-3'-azahexamethylene)urea
1-(2,6-dimethylphenylamidino)-3,3-(3'-oxapentamethylene)urea
1-(2,6-dimethylphenylamidino)-3,3-(2,'-thiatetramethylene)urea
1-(2,6-dimethylphenylamidino)-3,3-tetramethyleneurea
1-(p-fluorophenylamidino)-3,3-(α,α'-dimethylpentamethylene)urea
1-(2,6-dimethylphenylamidino)-3,3'-(α,α'-dimethylpentamethylene)urea
1-(2,6-dimethylphenylamidino)-3,3-(pentamethylene)urea
1-(2,6-dimethylphenylamidino)-3,3-(α-methylpentamethylene)urea
1-(N-methylamidino)-3-(2,6-dimethylphenyl)urea
1-(N-methylamidino)-3-(2,6-diethylphenyl)urea
1-amidino-3-(2-methyl-6-chlorophenyl)urea
1-amidino-3-(2-methyl-6-bromophenyl)urea
1-amidino-3-(2-methyl-6-methoxyphenyl)urea
1-amidino-3-(2,6-dimethylphenyl)urea
1-amidino-3-(2-methyl-6-ethylphenyl)urea
1-amidino-3-(2-ethyl-6-chlorophenyl)urea
1-amidino-3-(2,6-diethylphenyl)urea
1-amidino-3-methyl-3-(2-methyl-6-chlorophenyl)urea
1-amidino-3-methyl-3-(2-methyl-6-bromophenyl)urea
1-amidino-3-methyl-3-(2-methyl-6-methoxyphenyl)urea
1-amidino-3-methyl-(2,6-dimethylphenyl)urea
1-amidino-3-methyl-3-(2-methyl-6-ethylphenyl)urea
1-amidino-3-methyl-3-(2-ethyl-6-chloropyenyl)urea
1-amidino-3-methyl-3-(2-ethyl-6-bromophenyl)urea
1-amidino-3-methyl-3-(2-ethyl-6-methoxyphenyl)urea
1-amidino-3-methyl-3-(2,6-diethylphenyl)urea
1-amidino-3-(2-methyl-6-chlorophenyl)urea
1-amidino-3-(2-methyl-6-bromophenyl)urea
1-amidino-3-(2,6-dimethyl-4-hydroxyphenyl)urea
1-amidino-3-(2,6-dimethyl-3-hydroxyphenyl)urea
1-amidino-3-(2,6-dimethyl-3,4-dihydroxyphenyl)urea
1-amidino-3-(2,6-dimethyl-3,4,5-trihydroxyphenyl)urea
1-amidino-3-(2,6-dimethyl-4-methoxyphenyl)urea
1-amidino-3-(2,6-dimethyl-3-methoxyphenyl)urea
1-amidino-3-(2,6-diemthyl-3,4-dimethoxyphenyl)urea
1-amidino-3-(2,6-dimethyl-4-ethoxyphenyl)urea
1-amidino-3-(2,6-dimethyl-4-ethoxyphenyl)urea
1-amidino-3-(2,6-dimethyl-3,4-diethoxyphenyl)urea
1-(2,6-dimethyl-4-hydroxyphenyl)-3-methylamidinourea
1-(2,6-dimethyl-3-hydroxyphenyl)-3-methylamidinourea
1-(2,6-dimethyl-3,4-dihydroxyphenyl)-3-methylamidinourea
1-(2,6-dimethyl-4-methoxyphenyl)-3-methylamidinourea
1-(2,6-dimethyl-3-methoxyphenyl)-3-methylamidinourea
1-(2,6-dimethyl-3,4-dimethoxyphenyl)-3-methylamidinourea
1-(2,6-dimethyl-4-ethoxyphenyl)-3-methylamidinourea
1-(2,6-dimethyl-3-ethoxyphenyl)-3-methylamidinourea
1-(2,6-dimethyl-3,4-diethoxyphenyl)-3-methylamidinourea
1-amidino-3-(2,6-dimethylphenyl)urea
1-amidino-3-(2-methyl-6-ethylphenyl)urea
1-amidino-3-(2-ethyl-6-chlorophenyl)urea
1-amidino-3-(2-ethyl-6-bromophenyl)urea
1-amidino-3-(2-ethyl-6-methoxyphenyl)urea
1-amidino-3-(2,6-diethylphenyl)urea
1-amidino-3-methyl-3-(2-methyl-6-chlorophenyl)urea
1-amidino-3-methyl-3-(2-methyl-6-bromophenyl)urea
1-amidino-3-methyl-3-(2-methyl-6-methoxyphenyl)urea
1-amidino-3-methyl-3-(2,6-dimethylphenyl)urea
1-amidino-3-methyl-3-(2-methyl-6-ethylphenyl)urea
1-amidino-3-methyl-3-(2-ethyl-6-chlorophenyl)urea
1-amidino-3-methyl-3-(2-ethyl-6-bromophenyl)urea
1-amidino-3-methyl-3-(2-ethyl-6-methoxyphenyl)urea
1-amidino-3-methyl-3-(2,6-diethylphenyl)urea
1-(2,6-dichlorophenylamidino)-3-n-propylurea
1-(2,6-dimethylphenyl)-3-(isopropylamidino)urea
1-(4-bromo-3-chloro-6-methylphenyl)-3-methylamidinourea
1-(2-bromo-6-methylphenyl)-3-methylamidinourea
1-(2,6-dimethylphenyl)-3-(N-methyl-N'-propylamidino)urea The amidinoureas of Formulae I to V and their pharmaceutically acceptable salts are useful as feed efficiency agents. The antimotility activity and enhanced food nutrient digestion and absorption activity of these amidinoureas have been demonstrated for representative compounds within the class of compounds defined by Formulae I to V inclusive.

Among the tests which demonstrate the usefulness of those compounds in accordance with this invention are the following:

Gastric Emptying

The gastric emptying test is performed essentially as described by Brodie. Male Sprague-Dawley rats (groups of five) are dosed orally with the test compounds 30 minutes before the oral administration of 30 Amerlite pellets (Rohm & Haas Amberlite 1RA-93, 1 mm diameter) suspended in 1 ml distilled water. The animals are killed with pentobarbital four hours after the pellets are given, the stomachs are removed and the number of pellets remaining in the stomachs are counted. The control group is compared to the drug treated group using the following formula: %retention = [(mean drug-treated)-(mean control)]/[30-(mean control)]

TABLE I

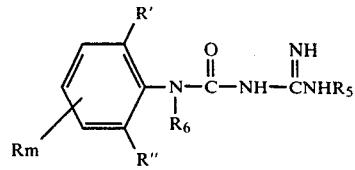

| R' | R'' | Rm | $R_6$ | $R_5$ | Dose mg/kg | % Inhib. |
|---|---|---|---|---|---|---|
| $CH_3$ | H | H | H | H | 10 | 54 |
| H | H | 4$NO_2$ | H | H | 10 | 59 |
| Cl | H | 4-Cl | H | H | 10 | 85 |
| H | H | 3-Cl, 4-Cl | H | H | 10 | 74 |
| $CH_3$ | H | 4-Cl | H | H | 10 | 28 |
| Cl | H | 4-$CH_3$ | H | H | 10 | 40 |
| Cl | Cl | 4Br | H | H | 40 | 54 |
| $CH_3$ | $CH_3$ | 4-$CH_3$ | H | H | 10 | 45 |
| Cl | F | H | H | H | 0.25 | 60 |
| Cl | Cl | H | H | H | 0.125 | 54 |
| Cl | $CH_3$ | H | H | H | 0.25 | 43 |
| $OCH_3$ | $CH_3$ | H | H | H | 0.5 | 70 |
| $CH_3$ | $CH_3$ | H | H | H | 0.25 | 55 |
| ET | $CH_3$ | H | H | H | 0.5 | 30 |
| ET | ET | H | H | H | 2.5 | 83 |
| $CH_3$ | $CH_3$ | H | $CH_3$ | H | 2 | 55 |

Charcoal Motility

A charcoal suspension (10 ml/kg of a 10% suspension of activated charcoal, U.S.P. in 0.5% methylcellulose) is given orally either to groups of 10 Swiss-Webster male mice (18–22 g, Taconic Farms) or groups of 5 Sprague-Dawley male rats (120–140 g, Charles River Breeding Labs., Inc.) 30 minutes after an oral dose of drug or vehicle. The animals are sacrificed 30 minutes after receiving the charcoal and the intestines are carefully removed without stretching and placed lengthwise on moist paper. The length of the intestine (pyloric sphincter to caecum) and the distance traveled by the charcoal as a fraction of that length are evaluated for each animal and group means are compared and expressed as percentage inhibition.

$$\% \text{ inhibition} = \frac{(\text{mean distance in controls}) - (\text{mean distance in treated})}{\text{mean distance in controls}} \cdot 100$$

For estimation of the duration of inhibition, the interval between dosing with drug and the administration of charcoal is varied from 30 minutes to 6 hours.

TABLE II

| R' | R'' | Rm | $R_6$ | $R_5$ | Dose mg/kg | % Inhib. |
|---|---|---|---|---|---|---|
| $CH_3$ | H | H | H | $CH_3$ | 4 | 11 |
| H | H | 4-$NH_2$ | H | ET | 4 | 20 |
| $CH_3$ | $CH_3$ | 3Br | H | $CH_3$ | 4 | 22 |
| $CH_3$ | $CH_3$ | 4-$CH_3$ | H | n-Pr | 4 | 15 |
| Br | Br | H | H | H | 4 | 91 |
| Br | $CH_3$ | H | H | H | 4 | 89 |
| $CH_3$ | $NO_2$ | H | H | H | 4 | 82 |
| Cl | $CH_3$ | H | $CH_3$ | H | 4 | 82 |
| $CH_3$ | $CH_3$ | H | n-Bu | H | 4 | 72 |
| ET | ET | H | $CH_3$ | H | 4 | 12 |

Studies on poultry conducted under strict laboratory conditions, that is, in a disease and parasite-free environment, indicate that the administration of the feed efficiency agents, such as, the amidinoureas defined in Formulae I-V, and, in particular, 1-(2,6-dimethylphenyl)-3-methylamidinourea, results in an increase in feed conversion ratio, and weight gain of the treated animal relative to that of the control animals. The feed conversion ratio, defined as the $$\frac{\text{Body Weight Gain of Treated Group}}{\text{Feed Consumption of Treated Group}} \div \frac{\text{Body Weight Gain of Control Group}}{\text{Feed Consumption of Control Group}} \times 100$$

is observed as being improved in the treated animals by a factor of up to about 10%, and averaged over a five week period of up to about 5%.

In addition to the amidinoureas illustrated above as suitable feed efficiency agents for use in accordance with the method of this invention, other compounds possessing antimotility activity and lacking growth retardant properties such as diphenoxylates and loperamide can also be used. Moreover, any one or more of these agents, including the amidinoureas, can be used in combination, It should be understood that compounds which have antimotility activity but which possess additional properties which act to retard digestion and absorption of feed nutrients are not encompassed within this invention.

The feed efficiency compounds can be utilized in accordance with this invention to achieve increased feed efficiency in food-producing animals by simply administering an effective amount generally less than the therapeutic dose where the compound also has therapeutic effects. Ordinarily, a daily dose between about 1 ppm to 20 ppm in the daily ration is sufficient to substantially increase the food retention and produce higher feed efficiency than is achieved by the animal without the administration of the feed efficiency agent.

In a preferred embodiment, the amidinoureas of Formulae I-V are utilized in dosage amounts between about 0.005 and about 0.5 mg/kg, and most preferably about 0.01 and about 0.1 mg/kg daily, administered in the animals' feed intake. A particularly preferred compound is 1-(2,6-dimethylphenyl)-3-methylamidinourea administered in an amount between about 0.01 and about 0.1 mg/kg. The amidinoureas are suitable utilized as their edible acid addition salts, preferably the hydrochloride salt.

The compounds used as feed efficiency agents in accordance with this invention can be administered along with the animals' normal dietary intake or compounded with other food additives or food supplements. For example, where protein supplements are used, such as in feeding cattle and sheep, the feed efficiency agents can be incorporated into the protein supplement. The feed efficiency agents are preferably administered during the normal growth stage of the animals. The feed efficiency agents can also be fed directly to the animals with or without suitable diluents and other edible excipients, or they can be prepared in the form of powders, pellets and the like for distribution in the feed materials such as silage, oats, barley, bran and the like. They can also be combined with other feed supplements such as bonemeal, salt, trace minerals, vitamins, antibiotics, growth hormones, etc. The amount to be included in the animals' feed materials or in feed supplements can be portioned in accordance with the animals' feed ration such that the effective amount of the feed efficiency agent on a daily administration basis is incorporated into the animals' daily feed ration.

By way of example, calves, in their early to mid growth stage, will show better food utilization when about 0.5 to 10 milligrams, preferably 1 to 5 milligrams and more preferably about 1 to 2.5 milligrams of an antimotility feed efficiency agent, particularly an amidinourea of the type described in Formulae I to V, is uniformly distributed throughout one kilogram of the feed materials. The feed efficiency agents can also be administered via other means, either directly or in combination with liquid or solid feed supplements such as feed blocks, salt blocks, and the like.

A preferred means of making the feed efficiency agents of the present invention available to feeding animals is by the uniform distribution of the feed efficiency agent throughout the animal feed. This distribution is facilitated by the preparation of a feed additive premix containing a higher concentration of feed supplement than the animal feed per se. The premix, which may be added to the feed in a ratio of 1 lb premix to 1 ton feed, comprises from about 2 to about 4 g/kg of feed efficiency agent and an edible carrier, preferably animal feed. The premix may also contain additional feed supplements as discussed above, such as, antibacterial agents, antiparasitics and tranquilizers.

The compositions and method of this invention are useful for improving the feed efficiency of all animals grown for commercial food production purposes, including those animals which are grown for meat production such as cattle, sheep, hogs, rabbits, chickens, ducks, geese, turkeys, pheasants and the like, as well as those animals which are grown for production of other food or useful animal products such as diary products, eggs, wool, fur and the like. Use of the compositions and method of this invention will shorten the growth period when fed to animals during their growing stages thereby reducing the time from birth to slaughter for animals grown for products such as meat, furs and the like. When used with mature animals, the compositions and method of this invention reduce the animal feed requirement to maintain the animal at full productivity, including work animals such as horses. In all cases, the use of the compositions and the method of this invention provide a greater output of animal products relative to the amount of animal feed consumed than could be achieved by maintaining the animal at the same feed regimen without such agents for improving feed efficiency.

It should be understood that the examples given herein are by way of illustration only and are not to be construed as limiting the invention, which contemplates the administration of any compound possessing antimotility properties and enhanced feed nutrient digestive and absorptive activity to foodproducing animals which provide meat, milk, etc., particularly livestock and poultry, to obtain higher food production per unit of animal feed material consumed.

I claim:

1. In a process in which the feed efficiency of an animal population of poultry is increased the improvement comprising administering to said animal population, including in said population healthy animals, about 0.01 to about 0.1 mg/kg of animal body weight of a material which increases the dwell time of nutrient matter in the digestive tract of said animal, the administration of said material being for a period of time sufficient to effect an increase in the digestion and absorption of said nutrients over and above that which would have been effected had the animal not assimilated said material wherein said material is an amidinourea of the formula

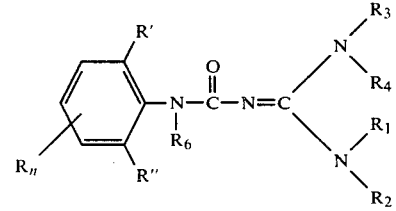

wherein $R_1$, $R_2$, $R_3$ and $R_4$ are hydrogen, halo lower alkyl, lower alkoxy, or lower alkyl; $R_6$ is hydrogen or lower alkyl; R' and R'' are hydrogen, lower alkyl, lower alkoxy, halo or halo lower alkyl; R is hydrogen, lower alkyl, halo, lower alkoxy, nitro, amino or halo lower alkyl and, n is 0–3; and, the edible salts thereof.

2. A process according to claim 1 including administering to said animal population one or more additives selected from the group consisting of antibacterials, antibiotics and antiparasitics.

3. A process according to claim 1 wherein said material is administered to said population in a non-therapeutic dosage amount.

4. A process according to claim 1 including administering to said animal population a non-therapeutic amount of said material and one or more additives selected from the group consisting of antibacterials, antibiotics and antiparasitics.

5. A method according to claim 1 wherein said material is an amidinourea of the formula:

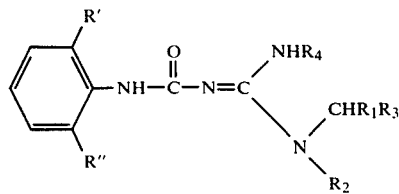

wherein $R_1$, $R_2$, $R_3$ and $R_4$ are hydrogen, lower alkyl, lower alkoxy or hydroxy; R' and R'' are hydrogen, halo or lower alkyl; and the edible salts thereof.

6. A method according to claim 5 wherein said amidinourea is 1-(2,6-dimethylphenyl)-3-methylamidinourea or an edible salt thereof in a dosage amount sufficient to increase the dwell time in the digestive tract of an animal feeding thereon.

* * * * *

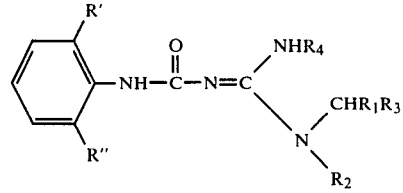

wherein $R_1$, $R_2$, $R_3$ and $R_4$ are hydrogen, lower alkyl, lower alkoxy or hydroxy; R' and R'' are hydrogen, halo or lower alkyl; and the edible salts thereof.

6. A method according to claim 5 wherein said amidinourea is 1-(2,6-dimethylphenyl)-3-methylamidinourea or an edible salt thereof in a dosage amount sufficient to increase the dwell time in the digestive tract of an animal feeding thereon.

* * * * *